United States Patent [19]

Macdonald

[11] Patent Number: 4,695,625
[45] Date of Patent: Sep. 22, 1987

[54] PROCESS FOR THE PREPARATION OF 16,17 ACETALS OF PREGNANE DERIVATIVES

[75] Inventor: Peter Macdonald, Arese, Italy

[73] Assignee: Sicor Società Italiana Corticosteroidi S.p.A., Milan, Italy

[21] Appl. No.: 739,131

[22] Filed: May 30, 1985

[30] Foreign Application Priority Data

Jun. 11, 1984 [IT] Italy ................................ 21343 A/84

[51] Int. Cl.$^4$ .............................................. C07J 71/00
[52] U.S. Cl. ....................................... 540/63; 540/68; 540/69; 540/70
[58] Field of Search ................ 260/239.55 D; 540/63, 540/68, 69, 70

[56] References Cited

U.S. PATENT DOCUMENTS 3,983,233  9/1976  Brattsand et al. ......... 260/239.55 D
4,404,200  9/1983  Thalen et al. .............. 260/239.55 D Primary Examiner—Leonard Schenkman
Assistant Examiner—Joseph A. Lipovsky
Attorney, Agent, or Firm—Walter H. Schneider

[57] ABSTRACT

A process for the preparation of 16,17 acetals of pregnane derivatives by trans-ketalization of 16,17-acetonides is described.

In the instance of the preparation of 16α,17α-butylidenedioxy-11β,21-dihydroxypregna-1,4-diene-3,20-dione, a compound having useful therapeutic properties, known also as budesonide, it is possible to obtain the more active epimer with high selectivity and remarkable economic advantages in comparison with the known methods.

New 16,17 acetals of pregnane derivatives, which can be prepared by the method of the invention, are also described.

11 Claims, No Drawings

PROCESS FOR THE PREPARATION OF 16,17 ACETALS OF PREGNANE DERIVATIVES

The present invention concerns a process for the preparation of 16,17 acetals of pregnane derivatives starting from the corresponding 16,17-acetonides.

More particularly, the process of the invention is conveniently applicable to the synthesis of 16α,17β-butylidendioxy-11β,21-dihydroxypregna-1,4-diene-3,20-dione, described in U.S. Pat. No. 3,929,768 and GB Pat. No. 1,429,922, a useful compound in human therapy, known also as budesonide, and to the synthesis of similar compounds.

Analogous compounds, which can be obtained by the process of the invention, are described also in the European patent application No. 0 054 010 of June 16th, 1982.

The invention refers moreover to new 16,17 acetals of pregnane derivatives, obtained according to said process.

The known methods for the preparation of said pregnene or pregnadiene 16,17 acetals are based upon the reaction of 16α,17α diols with aldehydes (butyraldehyde in the instance of budesonide) in the presence of acids and suffer therefore from the drawbacks connected with the use of 16α,17α diols, as starting materials, which are compounds difficult to prepare and purify and unstable because they tend to isomerize to D-homo-steriods. The known methods, moreover, do not exhibit any selectivity since the two epimers are obtained in almost equal amounts.

Moreover, said acetals exist as couples of epimers which can be separated with difficulty by means of cumbersome techniques which are difficult to be applied industrially, such as column chromatography, HPLC (high performance liquid chromatography) or gel-filtration as described in GB Pat. No. 1,428,416 and U.S. Pat. No. 3,928,326. Further, in the specific case of budesonide, one of the two epimers (hereinafter designated as "B") proved to be more active than the other one.

It is therefore evident the importance of an industrially applicable preparation method, which allows to obtain the preferred isomer with high selectivity and remarkably lower costs than that of the isomers mixture obtained according to the known process.

The process according to the present invention allows to overcome the drawbacks of the prior art and consists in a direct transketalization reaction with aldehydes on 16,17-acetonides, in the presence of hydrohalogen acids.

It is known that steroidal acetals or cyclic ketals can be hydrolized to diol compounds by treatment with aqueous HF or HCl, at temperatures ranging from −30° to +25° C. (U.S. Pat. No. Re. 26,877, 12-5-1970).

In the published German patent application No. 2,448,548 the preparation of 16,17 acetals or ketals starting from 9,11-epoxy-16,17-diols with aldehydes or ketones in the presence of hydrogen halides is described.

Quite surprisingly, with respect to the above cited documents and to what is known in the art, the method of the invention occurs in almost quantitative yields and, even more surprisingly, the more active epimer is almost exclusively obtained.

The steric selectivity can also be suitably controlled by changing the reaction conditions. Particularly, by changing the reaction temperature, it is possible to obtain products containing from 50% to more than 90% of the more active epimer (B epimer).

Another aspect of the present invention is the transformation of the less active epimer of a 16,17-acetal of pregnane derivatives into the more active epimer.

A further essential feature of the invention resides in the use, as starting materials, of 16,17-ketals, preferably 16,17-acetonides, which, differently from the 16,17-diol compounds up to now considered as the sole precursors for the preparation of the corresponding acetals, are stable, easily available compounds which can be easily purified. The acetonides, for the above cited reasons, are often used for the purification of diols and can be therefore considered to be precursors of the latter, and no vice versa, having moreover a lower production cost.

As a consequence, the process of the invention is particularly convenient, also leaving the exceptionally high yields obtained out of consideration, and it is possible to prepare new compounds previously impossible to be prepared because of the unavailability or the unstability of the corresponding diols.

The compounds which can be prepared by the process object of the invention have the following general formula:

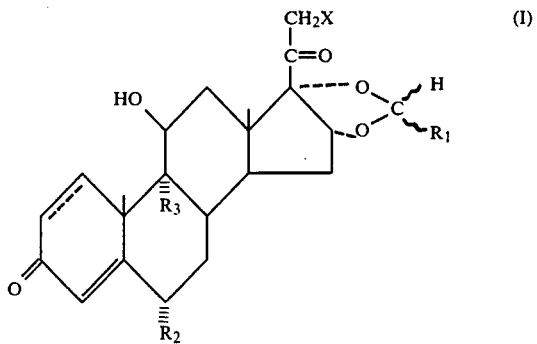

wherein
R₁ represents a $C_1$–$C_{12}$ alkyl group;
X may be OH, Cl, F or —OCOR groups wherein R represents a $C_1$–$C_{12}$ alkyl group;
R₂ may be hydrogen, fluorine or methyl;
R₃ may be hydrogen, fluorine or chlorine.
Many of the compounds of formula I are new and are comprised in the scope of the invention.

Particularly, new compounds according to the invention are:
6α-fluoro-16α,17α-butylidenedioxy-11β,21-dihydroxy-pregna-1,4-diene-3,20-dione;
9α-fluoro-21-chloro-16α,17α-butylidenedioxy-11β-hydroxypregna-4-ene-3,20-dione;
9α-chloro-16α,17α-butylidenedioxy-11β,21-dihydroxy-pregna-1,4-diene-3,20-dione;
6α-fluoro-16α,17α-butylidenedioxy-11β,21-dihydroxy-pregna-4-ene-3,20-dione;
9α-fluoro-16α,17α-butylidenedioxy-11β,21-dihydroxy-pregna-4-ene-3,20-dione;
21-acetoxy-16α,17α-butylidenedioxy-11β-hydroxy-pregna-4-ene-3,20-dione;
6α-fluoro-9α-chloro-budesonide 21-acetate;
6α,9α-difluoro-budesonide 21-acetate.

According to the invention, the 16,17-acetonides are reacted with aldehydes having formula R₁CHO, in molar ratios ranging from 1:1 to 1:5, preferably from 1:1 to 1:1.1, in aqueous hydrofluoric acid and concentrations ranging from 20 to 90%, preferably from 50 to 70%, at a temperature from −70° to 20° C., the temperature being choosen in order to give the desired epimer ratio.

The product is isolated by simple water dilution, in high purity.

Although working with unitary stoichiometric ratios between the steroidal substrate and the carbonyl compound, the reaction takes place in almost quantitative yields.

Alternatively, instead of hydrofluoric acid, it is possible to use hydrochloric acid. In this case, however, the reaction is less selective in the isomers ratio and the product obtained is less pure.

It should be noted that, in the process of the invention, the acetonide can be replaced by the corresponding diol derivative. Under these conditions the acetal is always produced with an excess of the B epimer, but with a lower selectivity.

Another aspect of the invention, equally important, concerns the conversion of the less active epimer of a 16,17-acetal into the more active epimer. For instance, a mixture of budesonide containing only 30% of the B epimer, subjected to the above mentioned conditions for the preparation of budesonide from the corresponding acetonide, is transformed into budesonide having more than 90% of B epimer. This process is very useful to recover active product from the mother liquors (as deriving from the crystallization) enriched in A epimer. For the epimerization of budesonide like compounds it is sufficient the treatment with hydrofluoric acid alone but, usually, an amount (lower than the stoichiometric one) of the aldehyde (in the instance of budesonide, butyraldehyde) is added in order to avoid any formation of the 16,17-diol.

The following non limiting examples further illustrate the invention. The designation "A epimer" or "B epimer" is made according to U.S. Pat. No. 3,928,326 and the epimer ratio was determined by HPLC using a reversed phase RP-18 column, eluting with 40% acetonitrile.

EXAMPLE 1

50 Grams of desonide (16α-hydroxyprednisolone-16,17-acetonide) and immediately thereafter 12,5 ml of butyraldehyde were added to 500 ml of a 70% hydrofluoric acid solution, at −5° C. The mixture was stirred at 0° C. for one hour and then poured into 5 liters of demineralized water at 0° C. The precipitate was filtered, washed to neutrality with water and dried under vacuum to give 51 g of pure budesonide with an A/B epimer ratio of 9/91.

EXAMPLE 2

The procedure described in Example 1 was repeated, except that the desonide was replaced by other acetonides. The corresponding acetals with butyraldehyde were obtained in almost quantitative yields and with the epimer ratios reported in the following Table.

TABLE

| Compound | Starting product | Final product | Ratio A/B epimer |
|---|---|---|---|
| 2a | Desonide 21-acetate | Budesonide 21-acetate | 13/87 |
| 2b | Triamcinolone acetonide | 9α-Fluoro-budesonide | 15/85 |
| 2c | Fluocinolone acetonide | 6α,9α-Difluoro-budesonide | 11/89 |
| 2d | Flunisolide | 6α-Fluoro-budesonide (6α-fluoro-16α-,17α-butylidenedioxy-11β,21-dihydroxypregna-1,4-diene-3,20-dione) | (Apparently only one epimer) |
| 2e | Flurandrenolide | 6α-Fluoro-16α,17α-butylidenedioxy-11β,21-dihydroxypregna-4-ene-3,20-dione | (Apparently only one epimer) |
| 2f | Alcinonide | 9α-Fluoro-21-chloro-16α,17α-butylindenedioxy-11β-hydroxy-pregna-4-ene-3,20-dione | 12/88 |
| 2g | 9α-Fluoro-16α,17α-isopropylidenedioxy-11β,21-dihydroxy-pregna-4-ene-3,20-dione | 9α-Fluoro-16α,17α-butylidenedioxy-11β,21-dihydroxypregna-4-ene-3,20-dione | 9/91 |
| 2h | 21-Acetoxy-16α,17α-isopropylidenedioxy-11β-hydroxypregna-4-ene-3,20-dione | 21-Acetoxy-16α,17α-butylidenedioxy-11β-hydroxypregna-4-ene-3,20-dione | 10/90 |
| 2i | 6α-Fluoro-9α-chloro-desonide 21-acetate | 6α-fluoro-9α-chloro-budesonide 21-acetate | 10/90 |
| 2j | Fluocinonide | 6α,9α-Difluoro-budesonide 21-acetate | ca.15/85 |

EXAMPLE 3

The procedure described in Example 1, was repeated, except that the reaction was carried out at −78° (and quenching the reaction after 12 hours at this temperature). Budesonide was obtained (A/B ratio 47/53) together with unreacted desonide (about 40%).

EXAMPLE 4

The procedure described in Example 1 was repeated, substituting butyraldehyde by isobutyraldehyde. 16α-Hydroxyprednisolone 16,17-acetal, apparently only one epimer, was obtained.

EXAMPLE 5

Under the same conditions as in Example 1, but using 16α-hydroxyprogesterone instead of desonide, budesonide was obtained (A/B ratio 16/84).

EXAMPLE 6

Under the same conditions as in Example 1, but using budesonide (A/B ratio 70/50) instead of desonide, budesonide having A/B ratio of 10/90 was obtained.

I claim:

1. A process for the preparation of 16,17-acetals of pregnane derivatives having formula I

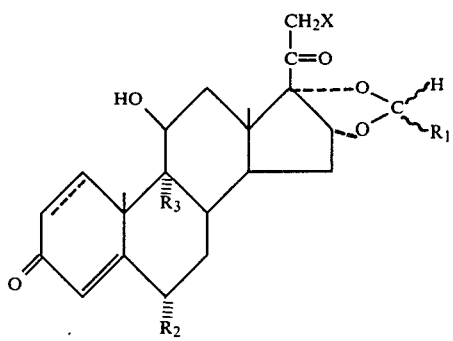

wherein
$R_1$ represents a $C_1$–$C_{12}$ alkyl group,
X may be OH, Cl, F or —OCOR group wherein R represents a $C_1$–$C_{12}$ alkyl group;
$R_2$ may be hydrogen, fluorine or methyl;
$R_3$ may be hydrogen, fluorine or chlorine;
characterized in that the corresponding 16,17-acetonides are reacted with aldehydes having formula $R_1$CHO, wherein $R_1$ has the same meaning as in formula I, in aqueous hydrofluoric or hydrochloric acid.

2. The process according to claim 1 characterized in that the molar ratio between steroidal acetonide and aldehyde ranges from 1:1 to 1:5.

3. The process according to claim 2 characterized in that the molar ratio between steroidal acetonide and aldehyde ranges from 1:1 to 1:1.1.

4. The process according to claim 3 characterized by carrying out the reaction in aqueous hydrofluoric acid and in concentrations ranging from 20 to 90%.

5. The process according to claim 4 characterized by carrying out the reaction in aqueous hydrofluoric acid, in concentrations ranging from 50 to 70% and at temperatures from −10° to 0° C.

6. A process according to claim 1 for the preparation of the B epimer of 16α,17α-butylidenedioxy-11β,21-dihydroxypregna-1,4-diene-3,20-dione (budesonide) characterized by reacting equimolar amounts of butyraldehyde and 16α,17α-isopropylidenedioxy-11β,21-dihydroxypregna-1,4-diene-3,20-dione (desonide).

7. The process according to claim 6 characterized by carrying out the reaction in aqueous hydrofluoric acid.

8. The process according to claim 6 characterized by carrying out the reaction in aqueous hydrochloric acid.

9. A process according to claim 1 for the preparation of the B isomer of pregnane acetal derivatives having formula I characterized in that the corresponding A epimer is reacted with aqueous hydrofluoric acid.

10. The process according to claim 9 characterized by carrying out the reaction in the presence of the corresponding aldehyde with molar ratios ranging from 0.1 to 1.0 moles/mole of acetal.

11. The process according to claim 10 for the preparation of the B epimer of budesonide starting from the corresponding A epimer.

* * * * *